United States Patent
Blum

(10) Patent No.: US 6,663,896 B1
(45) Date of Patent: Dec. 16, 2003

(54) DELAYED RELEASE ASPIRIN FOR VASCULAR OBSTRUCTION PROPHYLAXIS

(76) Inventor: Alvin S. Blum, 2350 Del Mar Pl., Fort Lauderdale, FL (US) 33301

( * ) Notice: Subject to any disclaimer, the term of this patent is extended or adjusted under 35 U.S.C. 154(b) by 37 days.

(21) Appl. No.: 09/920,018

(22) Filed: Aug. 1, 2001

(51) Int. Cl.[7] ............................. A61K 9/24; A61K 9/50; A61K 9/14; A61K 9/22
(52) U.S. Cl. ....................... 424/490; 424/489; 424/470; 424/458; 424/473; 424/468; 424/480; 424/481; 424/482; 424/494; 424/497
(58) Field of Search .................... 424/489, 490, 424/470, 458, 473, 468, 480, 481, 482, 497

(56) References Cited

U.S. PATENT DOCUMENTS

| | | | |
|---|---|---|---|
| 3,728,445 A | 4/1973 | Bardani | |
| 3,922,338 A | 11/1975 | Estevenel | |
| 4,562,061 A * | 12/1985 | Appelgren et al. | 424/32 |
| 4,687,660 A | 8/1987 | Baker | |
| 4,784,858 A | 11/1988 | Ventouras | |
| 4,857,337 A * | 8/1989 | Miller et al. | 424/480 |
| 4,970,081 A * | 11/1990 | Frisbee | 424/480 |
| 4,983,401 A * | 1/1991 | Eichel et al. | 424/473 |
| 5,112,621 A | 5/1992 | Stevens | |
| 5,238,686 A * | 8/1993 | Eichel et al. | 424/461 |
| 5,260,068 A | 11/1993 | Chen | |
| 5,260,069 A | 11/1993 | Chen | |
| 5,846,566 A * | 12/1998 | Burguiere et al. | 424/489 |
| 6,245,357 B1 * | 6/2001 | Edgren et al. | 424/473 |
| 2002/0044962 A1 * | 4/2002 | Cherukuri et al. | 424/459 |

* cited by examiner

Primary Examiner—Thurman K. Page
Assistant Examiner—Rachel M. Bennett
(74) Attorney, Agent, or Firm—Alvin S. Blum

(57) ABSTRACT

A method and controlled release oral unit dosage form of acetylsalicylic acid (aspirin) delays the release of the drug until a predetermined time interval after ingestion. This enables the drug to reach optimal therapeutic blood levels at a time in the early morning when the events leading up to a vascular obstruction culminating in a heart attack or stroke are most commonly occurring after the drug is taken in the evening. The convenience of taking the drug every evening should enhance compliance. By arranging for the optimal blood level to coincide with the peak incidence of strokes, a much smaller total dose of the drug may be used than is normally prescribed. This may reduce the incidence of side effects that are dose related. This will make the prophylactic use of aspirin available to more of the population.

14 Claims, No Drawings

DELAYED RELEASE ASPIRIN FOR VASCULAR OBSTRUCTION PROPHYLAXIS

BACKGROUND OF THE INVENTION

It is well known that sudden vascular obstructions, especially those causing heart attacks and strokes, can be prevented in many cases by regular oral doses of acetylsalicylic acid (ASA), commonly called aspirin. Unfortunately, ASA has serious side effects. It can be very irritating to the gastrointestinal tract, causing bleeding and ulceration. It can also lead to uncontrolled bleeding leading to hemorrhagic stroke. It has been shown that very small doses, such as 80 mg. every other day, can significantly reduce the incidence of cardiovascular occlusion. This regimen is not used as much as it should be used for several reasons. Many physicians are reluctant to prescribe the prophylactic use of ASA because of these side effects and also their potential liability. It is common to say, "do not take it if you are allergic to aspirin". Patients who have had discomfort after regular analgesic doses (650 mg.) are reluctant to use it. Also compliance with something that is to be taken every other day is hard to achieve.

Some features of ASA that may be useful we can infer from experience with the drug relative to heart attacks: 1) It is absorbed rapidly enough that it is effective in some cases if taken at the first sign of a heart attack. 2) Enough remains the second day after an 80 mg. dose to be effective in reducing heart attacks.

It would be useful to provide a form of aspirin that would have the maximum prophylactic value with minimal total dose. This would greatly reduce the side effects so that the benefits of the drug would be available to many more individuals. It would also be useful to find a form of the drug that would be easy to use to ensure compliance.

SUMMARY OF THE INVENTION

It is accordingly an object of the invention to provide a method and medicament formulation that will prevent vascular obstructions that lead to heart attacks and strokes with minimal side effects. The medicament is aspirin (ASA) or its derivatives. It is prepared in oral dose form to be taken at a convenient time in the evening, such as with the evening meal, or at bedtime. It is to be taken daily rather than on alternate days to enhance compliance. The dose is so prepared that, after ingestion, there will be no release of the drug into the gut in absorbable form for a preset time interval. The purpose is to ensure that the drug will reach an optimal blood level in the early morning when it is most needed. It is well known that the incidence of heart attacks is greatest in the morning. If the attack occurs at this time, the precipitating events occur somewhat earlier. By arranging to reach an optimal blood level of ASA to approximately coincide with the time when the need for the drug is greatest, the amount of drug administered can be greatly reduced. If 80 mg. is effective on the second day after administration when the blood level is very low, then a very low dose, such as 8 mg. or 16 mg., may be effective with this new formulation. Such a low dose would be easily tolerated with very low incidence of side effects.

These and other objects, features, and advantages of the invention will become more apparent when the detailed description is studied.

DETAILED DESCRIPTION OF PREFERRED EMBODIMENTS

The term aspirin as herein employed is meant to include acetylsalicylic acid (ASA) and derivatives thereof that have similar therapeutic effects.

The invention comprises the drug aspirin in oral dose form so formulated that it will release an insignificant amount of drug in absorbable form into the gastrointestinal tract for a preset time interval after ingestion of at least five to as much as eight hours. This is arranged so that the drug can be ingested the prior day, at dinner or bedtime. The drug is then absorbed from the gut over a time period arranged to most effectively elevate the blood level of the drug to a level that will coincide with the morning peak incidence of vascular obstruction commonly encountered.

Techniques are well known in the art for coating drugs with variously composed coating agents that dissolve very slowly in the intestine to delay release of the drug. Such coatings that delay release may be applied to pellets of ASA that are then enclosed in a capsule. All of the pellets may be coated to prevent release absorption before the preset time interval. Alternatively, the ASA maybe formed into a tablet that is then coated with a coating that dissolves slowly. Another well-known technique that may be used employs a coated tablet with a water-permeable but insoluble film. The film encloses an osmotic agent and the active ingredient. As water from the gut slowly diffuses through the film into the core, the core swells until the film bursts, releasing the drug. The film coating may be adjusted for selecting a suitable rate of water permeation, and thereby, ASA release time. In another embodiment, the tablet coating is impermeable, and water enters through a controlled aperture in the coating until the core bursts. When the tablet bursts, the contents may contain drug in freely absorbable form and some as sustained release pellets to release drug over a longer period of time, if desired.

These and other techniques may be employed to formulate tablets or capsules with the requisite time interval before aspirin release. The time interval may be between five and ten hours, for example. This time for optimal release may be earlier than the reported peak time of onset of heart attacks. Events occurring in the body that lead up to the actual heart attack such as activation of platelets, pooling and stagnation of blood in the extremities, dehydration, and the like may not lead to vascular occlusion in the presence of adequate blood levels of ASA. By administering the oral medication at a convenient time the previous night, the delay allows the drug to reach optimal levels when needed without disturbing a normal sleep pattern.

The method of the invention comprises administration of the low dose of the above composition in the evening with the time delay to release arranged to permit absorption into the blood in the early morning when it will be most effective in reducing the incidence of dangerous vascular obstructions.

While I have shown and described the preferred embodiments of my invention, it will be understood that the invention may be embodied otherwise than as herein specifically described, and that certain changes in form and arrangement and the specific manner of practicing the invention may be made within the underlying idea or principles of the invention.

What is claimed is:

1. A controlled release pharmaceutical composition in oral unit dosage form for releasing aspirin into the gastrointestinal tract in absorbable form at a predetermined time interval after ingestion and not before, the dosage form comprising:

a) a core comprising no more than 20 milligrams of aspirin;

b) a frangible coating of said core protecting said aspirin from dissolution by gastrointestinal fluids; and c) means incorporated in said dosage form for releasing said core into said gastrointestinal fluids after a predetermined time interval of at least five hours after ingestion, the composition releasing no aspirin into the gastrointestinal tract in absorbable form until the expiration of the time interval.

2. The dosage form according to claim 1 in which said means for releasing comprises:
   a) said coating having water permeable and water insoluble properties;
   b) said core further comprising a swelling agent having the property of increasing in volume on exposure to water; and
   c) in which said coating admits water at a predetermined rate that causes said swelling agent to swell until the coating bursts to release the core at said predetermined time interval.

3. The dosage form according to claim 1 in which said means for releasing comprises:
   a) said coating having water permeable and water insoluble properties;
   b) said core further comprising an osmotic agent having the property of dissolving in water,
       not passing through the coating and providing an osmotic effect when dissolved; and in which said coating admits water at a predetermined rate that causes said core volume to increase until said coating bursts to release said core at said predetermined time interval.

4. The dosage form according to claim 1 in which the core comprises no more than 10 milligrams of aspirin and the time interval is at least eight hours.

5. A method of providing a blood level of aspirin that does not begin to rise until a predetermined time interval of at least five hours after ingestion of a unit dosage form, the method comprising:
   a) providing a unit dosage form comprising:
       i) a core comprising no more than 20 milligrams aspirin;
       ii) a coating of said core protecting said aspirin from dissolution by gastrointestinal fluids; and
       iii) means incorporated in said dosage form for releasing said aspirin into said gastrointestinal fluids in absorbable form after a predetermined time interval of at least five hours after ingestion, during which time interval there is no release of aspirin in absorbable form into the gastrointestinal fluids.

6. The method according to claim 5, in which said means for releasing comprises:
   a) said coating having water permeable and water insoluble properties;
   b) said core further comprising a swelling agent having the property of increasing in volume on exposure to water; and
   c) in which said coating admits water at a predetermined rate that causes said swelling agent to swell until the coating bursts to release the core at said predetermined time interval.

7. The method according to claim 5, in which said means for releasing comprises:
   a) said coating having water permeable and water insoluble properties;
   b) said core further comprising an osmotic agent having the property of dissolving in water, not passing through said coating and providing an osmotic effect when dissolved; and
   c) in which said coating admits water at a predetermined rate that causes said core volume to increase until the coating bursts to release the core at said predetermined time interval.

8. A controlled release pharmaceutical composition in oral unit dosage form for releasing a drug into the gastrointestinal tract at a predetermined time interval after ingestion and not before, the unit dosage form comprising:
   a) no more than 20 milligrams of a drug selected from the group consisting of acetylsalicylic acid and its derivatives;
   b) a coating of said drug protecting said drug from dissolution by gastrointestinal fluids; and
   c) means incorporated in said unit dosage form for releasing said drug into said gastrointestinal fluids in absorbable form only after a predetermined time interval of at least five hours after ingestion, during which time interval there is no release of drug into the gastrointestinal fluids from the composition.

9. The unit dosage form according to claim 8 in which said drug comprises no more than 10 milligrams of said drug, and the time interval is at least eight hours.

10. The unit dosage form according to claim 8 in which said drug comprises no more than 5 milligrams of said drug, and the time interval is at least eight hours.

11. The unit dosage form according to claim 8 in which said drug comprises no more than 5 milligrams of said drug and the time interval is at least five hours.

12. The unit dosage form according to claim 8 in which said means for releasing comprises said coating being arranged to dissolve only after said predetermined time interval.

13. The unit dosage form according to claim 8 further comprising said drug being in the form of a plurality of pellets of said drug, with each pellet being coated with said coating, and the plurality of coated pellets being incorporated into a unit dosage capsule.

14. The unit dosage form according to claim 8 further comprising said drug being in the form of a plurality of pellets of said drug, with each pellet being coated with said coating, and the plurality of coated pellets being incorporated into a unit dosage tablet.

* * * * *